US011821768B2

(12) United States Patent
Hanay et al.

(10) Patent No.: US 11,821,768 B2
(45) Date of Patent: Nov. 21, 2023

(54) OBSERVATION OF FLOW-INDUCED INSTABILITY OF A NANO-MEMBRANE AND ITS USE FOR ON-CHIP FLUID AND AIR FLOW RATE SENSING

(71) Applicant: IHSAN DOGRAMACI BILKENT UNIVERSITESI, Ankara (TR)

(72) Inventors: Mehmet Selim Hanay, Ankara (TR); Arda Secme, Ankara (TR); Hadi Sedaghat Pisheh, Ankara (TR); Hatice Dilara Uslu Uslu, Ankara (TR); Mehmet Kelleci, Ankara (TR)

(73) Assignee: IHSAN DOGRAMACI BILKENT UNIVERSITESI, Ankara (TR)

( * ) Notice: Subject to any disclaimer, the term of this patent is extended or adjusted under 35 U.S.C. 154(b) by 384 days.

(21) Appl. No.: 17/243,994

(22) Filed: Apr. 29, 2021

(65) Prior Publication Data
US 2021/0341321 A1    Nov. 4, 2021

Related U.S. Application Data

(60) Provisional application No. 63/017,059, filed on Apr. 29, 2020.

(51) Int. Cl.
| G01F 1/66 | (2022.01) |
| G01F 25/00 | (2022.01) |
| G01F 25/10 | (2022.01) |
| A61M 16/00 | (2006.01) |

(52) U.S. Cl.
CPC .............. *G01F 1/662* (2013.01); *G01F 25/10* (2022.01); *A61M 16/0003* (2014.02); *A61M 2016/003* (2013.01)

(58) Field of Classification Search
CPC .......... G01F 1/662; G01F 25/10; G01F 25/13; G01F 1/66; A61M 16/0003; A61M 2016/003; A61M 2205/3334
See application file for complete search history.

(56) References Cited

U.S. PATENT DOCUMENTS

| 2016/0091544 A1* | 3/2016 | Daneshmand ......... G01N 22/00 |
| | | 324/633 |
| 2018/0143145 A1* | 5/2018 | Klein ..................... G01N 22/00 |
| 2018/0203080 A1* | 7/2018 | Acosta ................... G01N 24/08 |

* cited by examiner

*Primary Examiner* — Jermele M Hollington
*Assistant Examiner* — Zannatul Ferdous
(74) *Attorney, Agent, or Firm* — Crose Law LLC; Bradley D. Crose

(57) ABSTRACT

The present invention relates to a device wherein fluid or air-induced instability is converted into a flow sensing mechanism by building a CPW (Coplanar Wave Guide) resonator. Depending on the flow rate, periodic transitions between two bistable states emerge. Owing to the dependence of the transition period and the flow rate, the use of this effect for on-chip flow rate sensing is achieved with this invention. Moreover, the present invention ensures a flow rate sensor to be used in the ventilation machines for the treatment of the COVID-19 pandemic.

7 Claims, 8 Drawing Sheets

OBSERVATION OF FLOW-INDUCED INSTABILITY OF A NANO-MEMBRANE AND ITS USE FOR ON-CHIP FLUID AND AIR FLOW RATE SENSING

TECHNICAL FIELD OF THE INVENTION

The present invention relates to a device, a flow rate sensor, wherein fluid flow-induced instability on a nanomembrane is converted into a flow sensing mechanism by building a microwave resonator, the resonance frequency of which is influenced, preferably capacitively by the deflection of the nanomembrane. When a nanomembrane is subjected to fluidic flow, periodic transitions between different stable states emerge where the transition period depends on the flow rate. Owing to the dependence of transition period and the flow rate, the use of this effect for on-chip flow rate sensing is achieved with this invention. In addition to this first mechanism, two other flow rate sensor mechanisms are disclosed, based on the magnitude of the deflections. Moreover, the present invention constitutes a flow rate sensor to be used in the ventilation machines for the treatment of respiratory diseases as in the case of COVID-19 pandemic.

BACKGROUND OF THE INVENTION (PRIOR ART)

The interaction between fluid flow and micro/nanomechanical structures has attracted remarkable attention in recent years for understanding the dissipation mechanisms of and optimizing suspended microchannel resonators [1-3] and nanomechanical resonators working in an aqueous medium [4-6]. Fluid-structure interaction could also play an important role for microfluidic systems where there is a growing demand for flow sensors integrated on-chip. Interestingly, a constant flow rate can induce instability [7-9] on a mechanical element, an effect that can readily be observed in the fluttering of flags and papers.

In many biomedical microfluidics applications, accurate flow rate measurements on specified channels are critical, for instance, to control cell concentration in a test volume, modify the adhesion rate of cells on a substrate and sort particles with different sizes. In organ-on-a-chip and tumor-on-a-chip systems, cells are needed to be supplied with an optimal concentration of nutrients for maintaining their vitality. Furthermore, finely controlled doses of drugs should be administered to test the cellular response extracted from tumors [10,11]. In discrete microfluidics, droplets with well controlled sizes and compositions can only be generated by an exquisite control of different flow rates [12-14]. In most biomedical reactors, syringe pumps or peristaltic pumps are used to control flow rates however, these devices create delay and fluctuations affecting the studies negatively. Commercial flow sensors are still used outside the chip, generally in between the pumps and the chip. As a result, there is a strong need for robust on-chip flow sensors that can enable the flow rate measurements along specific microchannels.

Commercial flow rate sensors for microfluidics are based on different mechanisms such as thermal, capacitive, piezoresistive and optical sensing. Thermal sensors work by heating a region along the channel and measuring how fast heat is transferred through the convection of the fluid [15-18] which depends on flow rate. Thermal sensors do not require any moving parts and are relatively easy to fabricate. Capacitive sensors, composed of electrodes separated by a dielectric material, work by the alteration of electrode surface or dielectric material thickness [19]. Changes in magneto-impedance can be used [20] for flow sensing inspired by nature. In optical flow sensors, microbubble image velocimetry [20,21], microparticle velocimetry [23] and Doppler shifts of droplets through laser Doppler velocimetry have been used to measure flow rates [23,24]. Optofluidics sensors [26] measuring the deformation of a cantilever system due to drag force was also introduced with a minimum detectable flow rate of 1.3 µL/min.

With mechanical flow rate sensors [27] a cantilever-based sensor with holes having variable sizes is manufactured and flow rate fluctuations are correlated with cantilever deflection. This sensor works by passing the fluid through a perforated cantilever structure: the deflection of the cantilever is then used for quantifying the flow rate. While the measurement of flow rates at nL/min level is accomplished, the requirement of routing the flow through the exquisite mechanical structure complicates the fabrication. Moreover, the measurement of the perforated cantilever deflection necessitated the use of a microscope as the readout mechanism. Numerous types of integrated electrical resonator flow sensors operating in radiofrequency have been reported [29-31]. Recently, Zarifi et al. [30] presented flow rate sensor exploiting the quasi-static deflection of a thin PDMS layer and measured this deflection via a microwave integrated PCB circuit. This sensor's sensitivity is around 0.5 µL/min.

The current COVID-19 pandemic has shown an abundant need for ventilation machines which is essential to keep patients alive and maintain their treatment effectively. For these machines, the flow sensor is the most critical component as it adjusts the incoming oxygen level to patients in a finely and accurately. Due to the problems in the technical field, it is necessary to improve technology to overcome these problems.

SUMMARY OF THE INVENTION

The present invention discloses a device wherein fluid (e.g., liquid or gas) flow induced instability on a nanomembrane is converted into a flow sensing mechanism by probing a microwave resonator in close proximity whose resonance frequency depends on the deflection (displacement and/or deformation) of the nanomembrane. The microwave resonator is preferably fabricated entirely or partially on the nanomembrane so that the deflection of the nanomembrane induces a capacitance change on the microwave resonator, which is then measured as a change in resonance frequency.

In the present invention, liquid flow is investigated over a $Si_3N_4$ membrane with 220 nm thickness within a microfluidic system. At different flow rates, periodic deflections of the nanomembrane (defined hereafter as pulsations) are observed under an optical microscope. The period of these pulsations is observed to depend on the constant flow rate of the liquid. In order to convert this mechanism into an entirely electronic flow rate measurement, a microwave resonator is fabricated which partially overlapped with the nanomembrane. The periodic deflections of the nanomembrane were then detected as periodic changes in the resonance frequency of the microwave resonator, since the capacitance of the microwave resonator depends on the geometry of the nanomembrane. The advantage of using a microwave resonator is that the capacitance changes can be measured precisely. It is clear that any other capacitive measurement technique can also probe the periodic deflections of the membrane.

The aim of the present invention is to monitor fine and coarse flow rate sensing to show that different flow rate intervals can be spanned effectively. To this end, sensors with different membrane sizes are utilized to monitor fine and coarse flow rate sensing. The flow sensor shows sensitivity to minimum rate change increment of 0.1 µL/min with the lowest detection limit of 0.4 µL/min in a relatively larger membrane device. With this device, flow rates between 0-3.5 µL/min are examined. Flow rates up to 50 µL/min are observed in another sensor encompassing smaller membrane dimensions.

Another aim of the present invention is to achieve high sensitivity of flow rate measurement.

Another aim of the present invention is to develop a device to be used in the ventilation machines for the treatment of the COVID-19 pandemic.

Another aim of the present invention is to enable on-chip microfluidic components, such as pumps and valves, which can be controlled and/or actuated by the periodic deflections induced on the nanomembrane under constant fluid flow.

DESCRIPTION OF REFERENCES IN DRAWINGS

Figure 1:
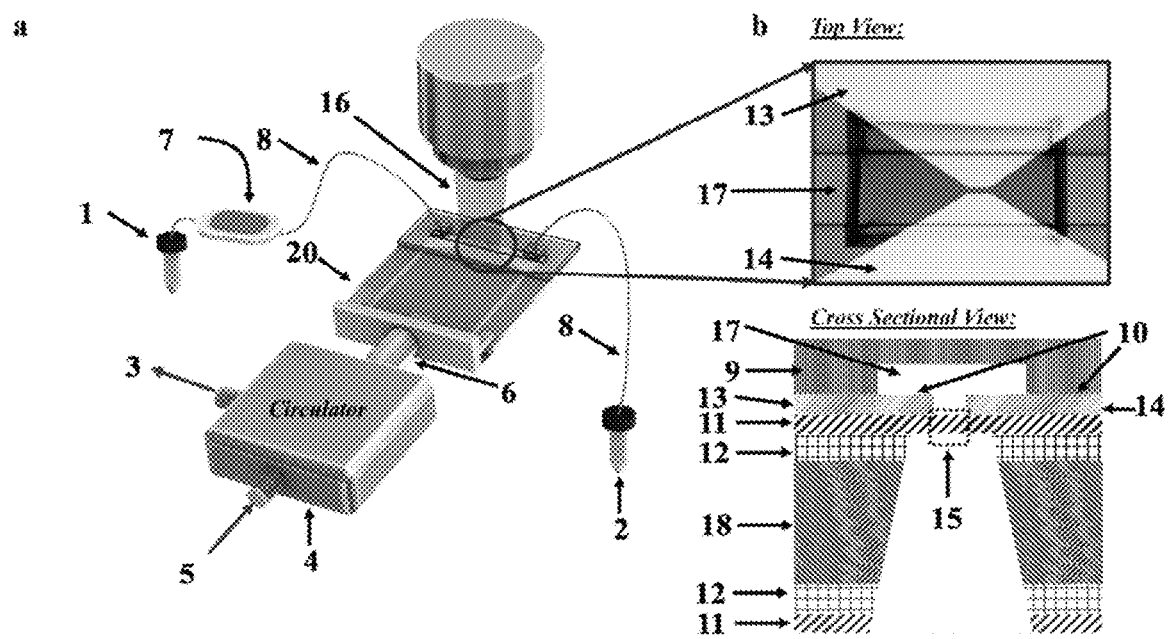
FIG. 1: (a) Experimental configuration of the subject-matter of device, (b) top view of the nanomembrane taken under an optical microscope and cross-sectional schematics of the fabricated device.

1. Reservoir
2. Waste
3. Output signal
4. Circulator
5. Input signal
6. Microwave signal
7. Reference flow sensor
8. Microfluidic Tubings
9. Polydimethylsiloxane (PDMS)
10. Gold
11. Silicon nitride ($Si_3N_4$)
12. Silicon dioxide ($SiO_2$)
13. Signal Electrode of the Microwave Sensor
14. Ground Electrode of the Microwave Sensor
15. Nanomembrane
16. Optical imaging
17. Microfluidic Flow Channel
18. Silicon (Si)
19. Pressure pump
20. Integrated Chip
21. Splitter
22. Signal Generator
23. RF Mixer
24. Low Pass Filter
25. Lock in amplifier
26. Photoresist

DETAILED DESCRIPTION OF THE INVENTION

The present invention discloses a device, a flow rate sensor, wherein fluid (e.g., liquid or air) induced instability on a nanomembrane (membrane having a sub-micrometer thickness) is converted into a flow sensing mechanism by building a microwave resonator whose resonance frequency depends on the geometry of the deflection. The membrane having a sub-micrometer thickness is useful for making the membrane compliant enough; clearly, any nanomembrane with sufficient compliance can be used for the same purpose.

The flow rate sensor subject to the invention comprises at least three essential parts:

A) a microfluidic flow channel (17) through which the fluid will flow

B) a nanomembrane, preferably a nanomembrane (15) which has sub-micrometer thickness, which interfaces with or forms part of the channel in (A), so that the fluid flow on (A) induces deformations on the nanomembrane, wherein the deformations take the form of:
   a. periodic oscillations (pulsations) at a constant flow rate with (i) oscillation period and (ii) magnitude dependent on the flow rate;
   b. or the deformations take the form of a (iii) sudden displacement when a reset flow rate (i.e., no flow condition) is suddenly increased to a set flow rate, C) a microwave resonator which is fabricated at close proximity, preferably on top of the nanomembrane (15), so that the different parameters of deformations (i), (ii) and/or (iii) induces impedance changes, preferably capacitance changes, on the microwave resonator which in turn changes the resonance frequency of the microwave resonator which can be probed continuously.

Thus, the fluid flow passing through a microfluidic channel (17) (microchannel) creates deformations with specific features in the nanomembrane (15) which then can be measured through the resonance frequency of the microwave resonator (C) to infer the fluidic flow rate. This way the entire assembly works as a flow rate sensor. If the deformation (i) is used to measure the flow rate, then it is labeled as first mechanism. If the deformation (ii) is used to measure the flow rate, then it is labeled as second mechanism. If the deformation (iii) is used to measure the flow rate, then it is labeled as third mechanism.

The fluid, whose flow rate is to be measured, can be a liquid or gas. All the three deformation features (i), (ii) and (iii) can be induced by both forms of fluids. It is clear that when working with gaseous material, since the inertial forces are relatively small due to the low density of gases with respect to liquids, it is more preferable to work with a more compliant membrane, meaning that the dimensions should be adjusted as such, for instance by decreasing the thickness of the membrane. It is also clear that for a targeted flow range of the fluid, whether in gas or fluid phase, the geometrical and material design of the membrane can be adjusted to optimize the deformation characteristics presented here, such as the pulsation period.

Preferably, the microwave resonator is patterned, partially or entirely, on the nanomembrane which deflects periodically upon constant flow rate within a microchannel. The microwave resonator is utilized to determine the flow rate by measuring the change in the resonance frequency, while the nanomembrane is utilized to convert fluid flow to a mechanical motion. The microwave resonator has preferably the form of a coplanar waveguide resonator with signal and ground electrodes fabricated on the nanomembrane, so that the deflection of the nanomembrane induces capacitance changes of the microwave resonator, which can be monitored with high precision through the resonance frequency.

Three distinct physical parameters of the nanomembrane, which can be probed by the microwave resonator, can be used for flow rate sensing. The first mechanism uses the period of pulsations of the nanomembrane at a given constant flow rate. The second mechanism uses the magnitude of the pulsations of the nanomembrane at a given constant flow rate. The third mechanism uses the magnitude of the frequency change of the microwave resonator between a set flow rate and a reset flow rate. The first and second mechanisms are sustained during a constant flow rate, whereas the third mechanism emerges when the flow rate switches between a reset and set conditions.

In the present invention, a novel flow rate sensor based on a microwave resonator integrated with a membrane with nanoscale thickness is disclosed. A microwave resonator is fabricated on-chip to detect the deflection of a nanomembrane under fluidic flow. In this specific embodiment of the invention, the microwave resonator has the form of a coplanar waveguide resonator with conductive surfaces made out of Gold (10), defining signal (13) and ground (14) electrodes. Parts of the signal and ground electrodes overlap with the nanomembrane made out of Silicon Nitride (11), supported on a Silicon wafer (12) and surrounded by PDMS (9) to define the microfluidic flow channel. Importantly, the distance between the signal (13) and ground (14) electrodes shrink down on the nanomebrane: the advantage of this design is that the capacitance, and therefore the resonance frequency, of the microwave resonator becomes, which depends on the distance between signal and ground electrodes, depends sensitively on the deflections of the nanomembrane.

A commercial flow sensor is used to independently verify the responsivity of the disclosed on-chip flow rate sensors. Specific pulse periods in phase and frequency response of the sensor are observed to change with flow rate. The flow rate tested here is spanned between 0-50 µL/min with two membranes with different sizes. According to the present invention, at each constant flow rate, the nanomembrane has 1) specific number of pulsations per unit time, and 2) the magnitude of shifts in the frequency of the microwave sensor. Each of these parameters, independently or together, can be used for flow rate measurements. The $1^{st}$ mechanism is shown to be capable of detecting flow rates down to 0.4 µL/min and sensitive enough to track flow increments of 0.1 µL/min. Owing to the materials used, the flow rate sensor has the advantage of being biocompatible, non-contact and non-intrusive. The demonstration of fluid-induced instability with nanomembranes paves the way for on-chip pumps, valves and other mechanisms which can couple different micro/nano fluidic channels.

Figure 6:
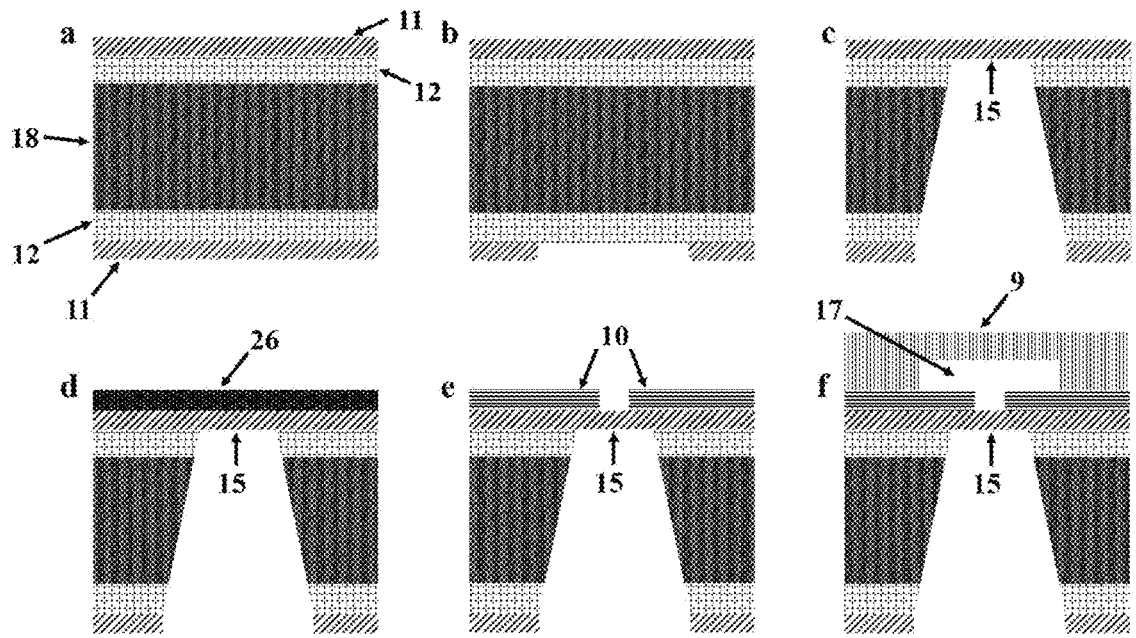
FIG. 6: Fabrication scheme of the device; (a) wafer used for fabrication, wherein the top layer is Silicon Nitride with 220 nm thickness, followed by an oxide layer, 2 µm thick, and then 500 µm thick Silicon wafer, (b) nitride layer at the bottom is plasma etched in order to open a window for membrane formation, (c) nitride membrane is suspended with KOH wet etching, (d) suspended membrane side of the wafer is UV exposed after spinning photo resist on it and resonator pattern is obtained. (e) gold layer is thermally coated and then left for lift off, (f) polydimethylsiloxane (PDMS) channel fabricated via soft lithography process is aligned manually and bonded on top of the electrodes & membrane (Bonding procedure is done by the oxygen plasma process.)

The fabrication, operation and verification of an embodiment of the flow rate sensor are described below. The fabrication of the sensor can be accomplished by standard micro/nano fabrication steps. A wafer consisting 500 µm Si at the core, 2 µm $SiO_2$ on top of Si and 220 nm SiN at the outer shell is used to fabricate the device. The topmost SiN eventually forms the membrane of interest (FIG. 6a). The backside of the wafer is first coated with a photoresist and then exposed to UV light with photolithography process to define a window. The window is etched by inductively coupled plasma (FIG. 6b) and left for overnight KOH wet etching (FIG. 6c). KOH etches through Si and $SiO_2$, and a 220 nm thick membrane forms at the front surface. The typical dimension for the fabricated membrane is around 600-1500 µmin length and 300-500 µmin width. Gold paths for generating CPW microwave resonator is patterned on the front side of the wafer. The photolithography mask is aligned according to the position of the thin film membrane and UV light is exposed (FIG. 6d). Then, 100 nm gold is coated in order to form the signal and ground electrodes (FIG. 6e). In order to reduce the losses due to impedance, the coplanar waveguide resonator is designed to have 50Ω characteristic impedance matching that of the electronic measurement system of the invention. The gap between ground and signal line is 400 μm which narrows down to 20 μm at the sensing region.

For the fabrication of the microfluidic flow channel (17), a negative photoresist is used to fabricate molds. Cured PDMS (ratio 10:1) is poured onto these molds and left for baking at 95° C. Microchannels, typically having dimensions of 300 μm in width and 150 μm in depth, are peeled off from the mold. Using plasma cleaning process, microchannels are bonded on top of the chip and aligned with membrane and gold electrodes (FIG. 6f).

To verify the correct operation of the proposed flow rate sensor, experiments were conducted in a setup that consisted of two major subsystems: a commercial microfluidic flow controller used as a reference and an electronic measurement system (FIG. 1). The chip is placed under the optical microscope stage to observe any possible mechanical deflection of the membrane (displacement and/or deformation). A microwave circulator is employed for driving and reading the electronic signal of the resonator. The nanomembrane is suspended through wet etching, then gold electrodes which form part of the microwave resonator are aligned on nanomembrane. PDMS microchannel is positioned on top of gold electrodes and membrane.

DI water is driven by a controllable pressure pump and passed through a thermal flow sensor before reaching to microfluidic channel on the chip. The flow sensor has a 430 μm ID borosilicate capillary and calculates the flow rate by combining two different temperature readings obtained from two different locations inside the capillary. In between these two temperature sensors, there is a micro heater and the flow rate value is calculated by the dissipation of the heat. The range of this sensor, calibrated with water, is 0-80 μL/min with an accuracy of 5% above 2.4 μL/min and 0.12 μL/min deviation below 2.4 μL/min. PTFE tubes are used to deliver DI water to the microchannel.

Figure 7:
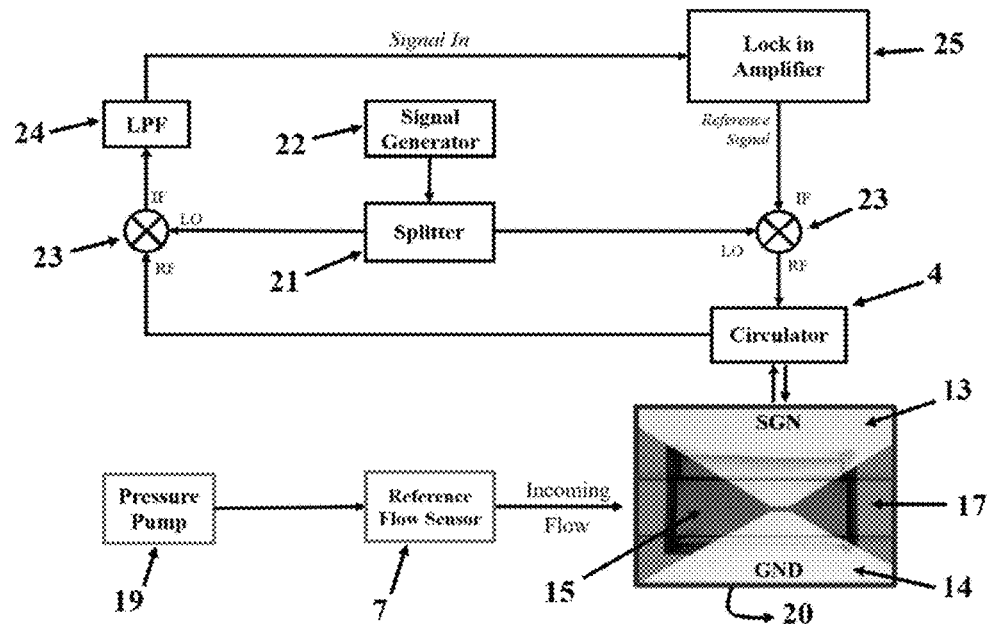
FIG. 7: Experimental setup and custom-built electronic measurement circuitry.

A narrow-band detection scheme, which is centered around the first resonance frequency of the CPW structure, is utilized to increase the sensitivity of the microwave sensor. Phase-sensitive detection is performed with a lock-in amplifier. Due to the frequency upper limitation of the lock-in amplifier, an external heterodyne circuitry is constructed to continuously track the resonance frequency (FIG. 7). With Phase Locked Loop (PLL), the phase of the resonator was locked to 0 degrees with a PI controller. Any deviation from 0 degrees emerged as an error signal updating the frequency of the signal generator. With this method, microwave resonator is effectively kept at its resonance frequency.

In the first experiment, while tracking the resonance frequency of the microwave resonator at 2.83 GHz, the flow rate was increased or decreased stepwise while recording changes in the resonance frequency. Data acquisition was done by custom-built LabVIEW structure where electronic data and flow rate values from sensor were recorded simultaneously every 50 msec.

Figure 2:
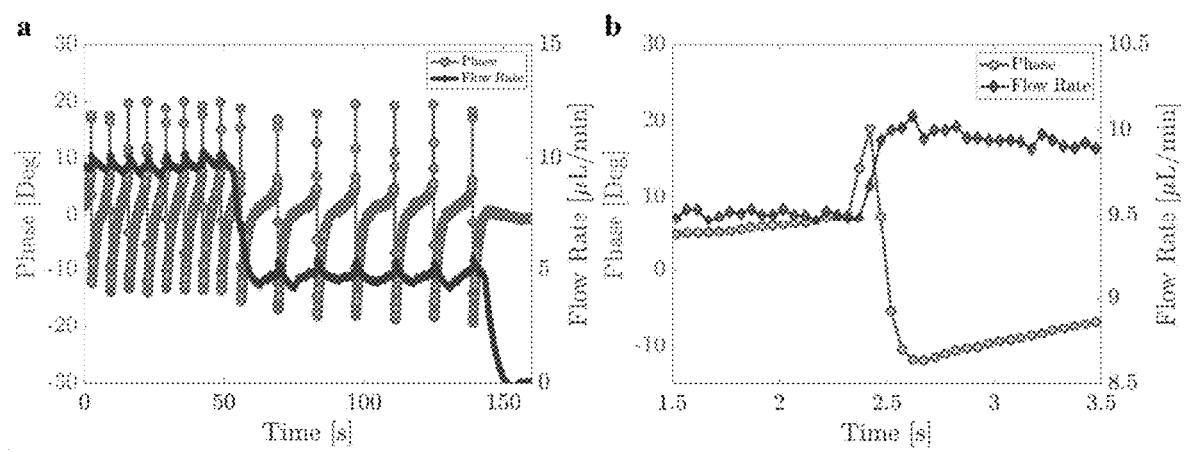
FIG. 2: (a) An example time-trace of pulsation behavior of the sensor, (b) Zoomed to event sequence. First, the membrane deflects inducing a change in the phase of the microwave sensor, then a follow-up perturbation occurs in the flow rate sensor.

An example of induced modulation is illustrated in FIG. 2. The figure shows the relation between the phase response of the resonator and the effective flow rate. Two different flow rates, 10 to 5 μL/min, are shown in the test: for each flow rate, the time between two consecutive pulses, called pulse interval ($T_i$), remains constant. As the flow rate decreases, it was observed that pulse intervals dilate. When flow rate is set to 10 μL/min, pulse interval $T_1$ is around 7 seconds whereas at 5 μL/min flow rate, pulse interval $T_2$ rises to 14 seconds. Therefore, the change in the reference flow rate results in a change in the pulsation period of the nanomembrane.

Microwave response and flow rate obtained from the reference flow sensor are measured and recorded simultaneously (FIG. 7). Pulse intervals vary as the corresponding flow rate changes. The response for the microwave sensor depends on the deformation of the elastic membrane. As the membrane deflects, the distance between signal and ground electrodes changes which results in a capacitance variation of the microwave resonator. Although the exact mechanism behind fluid-induced instability and pulsations is still under investigation, the same behavior is observed in different devices. The small peaks in the flow rate (as measured by the sensor) occur right after the pulsation also strengthens this hypothesis (FIG. 2b) since a deflected membrane results in an enlarged channel which then reduces the channel resistance and causes an increase in the flow rate driven under constant pressure conditions.

Figure 3:
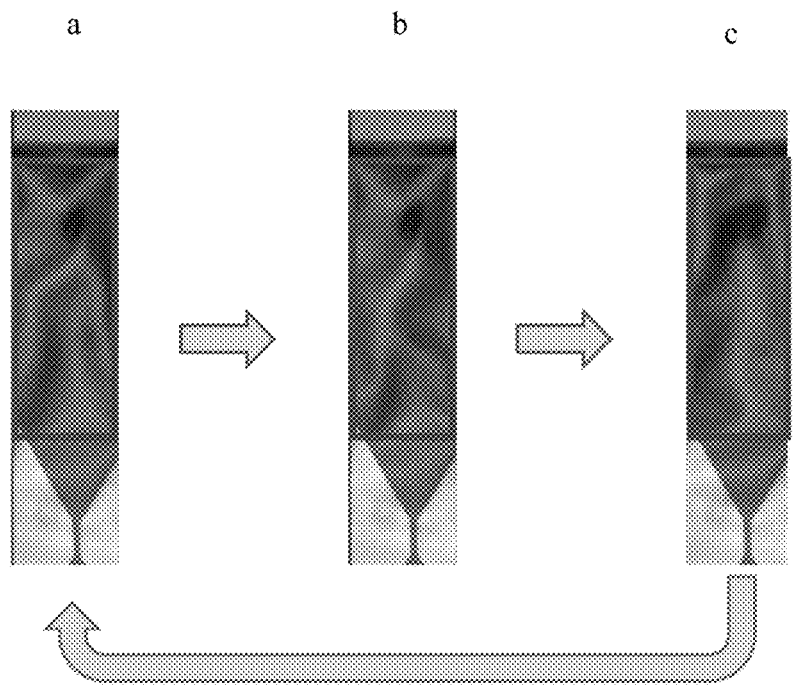
FIG. 3: The observation of pulsations of a nanomembrane under optical microscopy, wherein three distinct states during the pulsation are shown in this figure: a) stable state 1, b) metastable state, c) stable state 2.

To further verify that the pulsation seen by the microwave sensor under constant flow rate originates from the instability of the membrane, the experiments were performed using larger and more compliant membrane at higher flow rates. Optical microscopy imaging (FIG. 3) clearly indicates the cyclic deformation of the membrane. Three different states of the nanomembrane deformation can be identified in FIG. 3 with two stable states and one intermediate, metastable state. The upper part of the membrane shuttles between Stable State 1 and Stable State 2. The duration of this shuttling depends on the fluid flow inside the microchannel. The membrane used for this visualization had dimensions of 1.5 mm×0.3 mm with 220 nm thickness. The period of transitions between states and pulsation periods matches each other. Thus, it is concluded that the pulsations indeed originate from the microscale mechanical deformation of the membrane induced by the fluid flow. Hence, the proposed mechanism, a nanomembrane, (a membrane with sub-micrometer thickness), coupled to a microwave resonator, can be used for flow rate measurements integrated on-chip.

Figure 4:
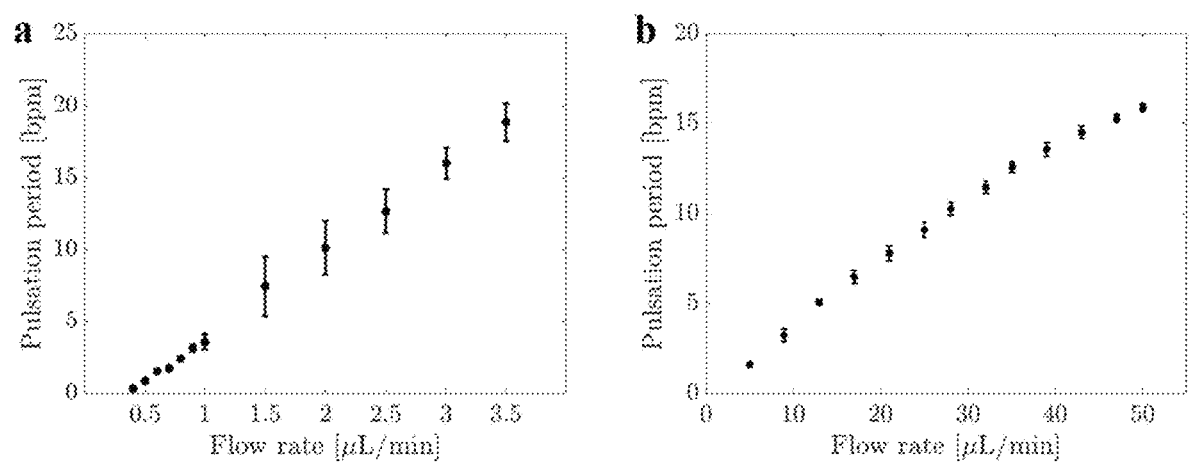
FIG. 4: The period of pulsations with increasing flow rate; (a) the response of the device with a larger membrane which can be used for more delicate measurement of flow rate, (b) the response of another device with different dimensions which can be used to for the measurement of flow rate spanning a large range.

After initial observations, various swept flow rates have been tested by using two different devices with membranes of different sizes (FIG. 4). In order to enhance the sensitivity of the resonator, a large membrane (1.5 mm×0.3 mm×220 nm) is fabricated and used for resolving slight increments in the flow rate. The resonance frequency of this device was 3.66 GHz. In FIG. 4a, the flow rate is set to an interval of 0-1 μL/min with an incremental change of 0.1 μL/min via the reference sensor. Until 0.3 μL/min, the device did not register any pulsation in the resonance. In fact, the reference flow sensor which is used to set the flow rate of the pump does not work well at this low flow rate: for a 0.3 μL/min set value, the error in the flow sensor is ±0.12 μL/min. Therefore, the flow condition at these small values is not reliably controlled due to the limitations of the sensor. However, the absence of the pulsation might also be related to the critical flow speed. After reaching a flow rate of 0.4 μL/min, the device started to give discernible pulses. Then, the flow rate increment was changed to 0.5 μL/min and it was spanned until 3.5 μL/min. FIG. 4a indicates an almost linear correlation between the flow rate and the number of pulsations. In another realization of the same device with different dimensions (800 μm by 350 μm by 220 nm, length, width, thickness respectively) and a microwave resonance frequency of 2.36 GHz, was used to span a higher flow rate range. The flow rate was started from 5 μL/min and recorded pulses for 300 seconds at each flow rate value. Then, the current flow rate was increased with 5 µL/min steps and flow rate of 50 µL/min have been reached. A similar trend, compared to the trend depicted in FIG. 4a, was observed with this device (FIG. 4b). From FIGS. 4a and 4b, it is clear that for a given device, a specific pulsation period corresponds to a specific flow rate value.

FIG. 4 reflects that, apart from effective flow rate, the size of the membrane is a crucial factor affecting the working mechanism of these on-chip microwave flow sensors. The number of pulsations is denoted here in the unit of a beat per minute (bpm). For instance, when FIGS. 4a and 4b are compared, 10 bpm is achieved with 2 µL/min for the device with larger membrane area (1.5 mm×0.3 mm), whereas the same number of beats is achieved at 30 µL/min for the device with smaller membrane area (800 µm×350 µm). Therefore, sensors with different geometries can be designed for different target flow ranges. Similarly, flow sensors can be manufactured according to the intended flow rate with alternating flow ranges.

Figure 10:
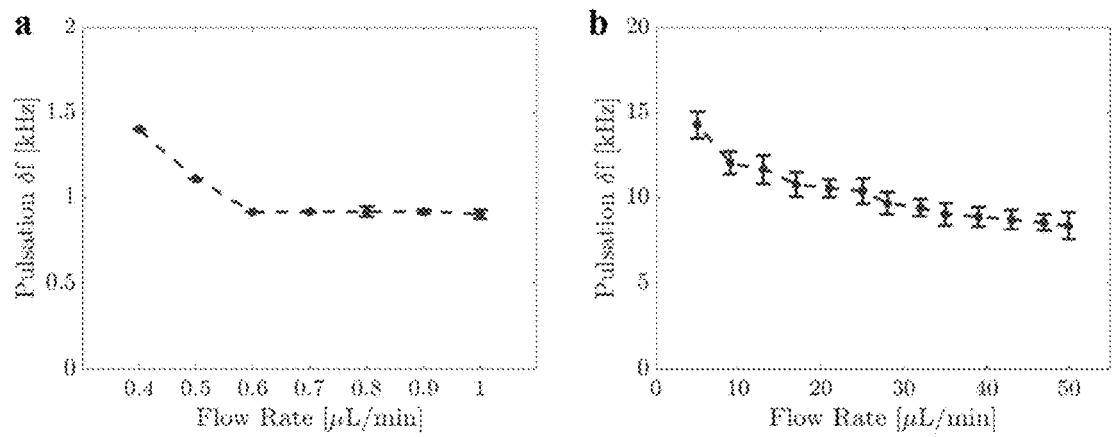
FIG. 10: Trends of frequency shifts during pulsations (second mechanism); (a) the magnitude of the pulsation frequency δf remains mostly stable with the device of FIG. 8, (b) data taken with the device of FIG. 9 follows a decreasing trend.

The amount of frequency shift during pulsations is also specific to the effective flow rate (FIG. 10). For small increments in the flow rates (0.1 µL/min), frequency shifts do not vary remarkably (FIG. 10a); however, for larger incremental steps, e.g., 5 µL/min, a downward trend in the frequency modulations is evident (FIG. 10b).

Figure 5:
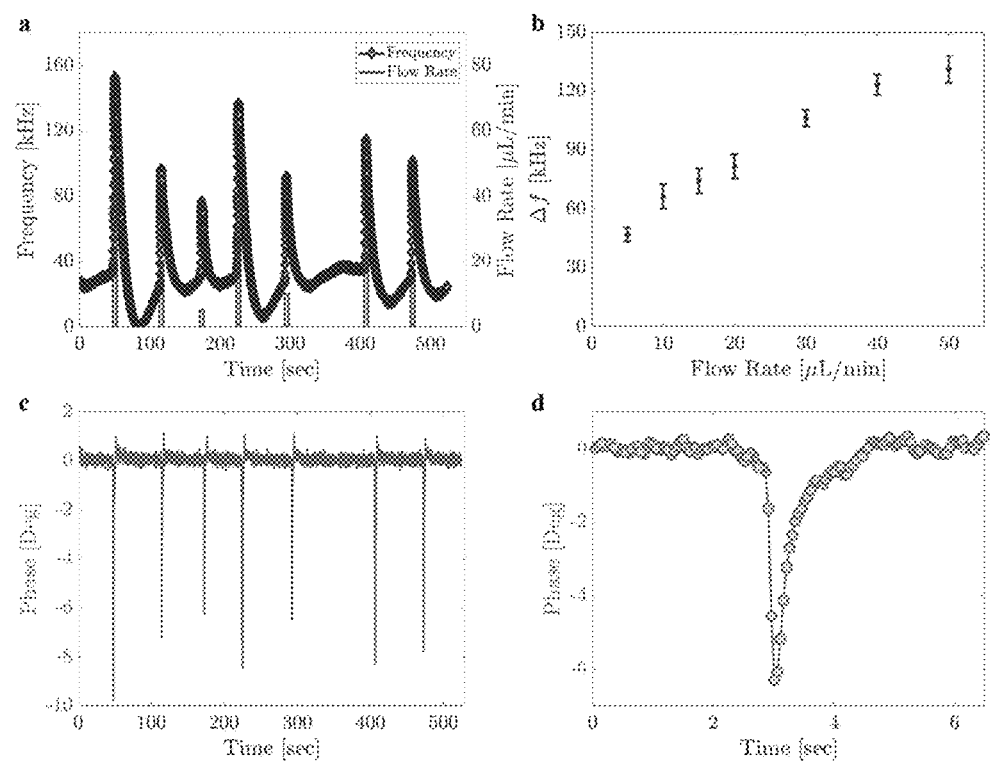
FIG. 5: (a) The frequency change of the microwave resonator at target flow rates measured with respect to reset fluid flow, (b) the magnitude of frequency changes against target flow rate wherein the frequency shifts show monotonically increasing behavior), (c) the change in the phase response of the microwave resonator, at the same conditions as in part a, (d) the phase of the resonator shows negligible relaxation time to fluid flow.
Figure 11:
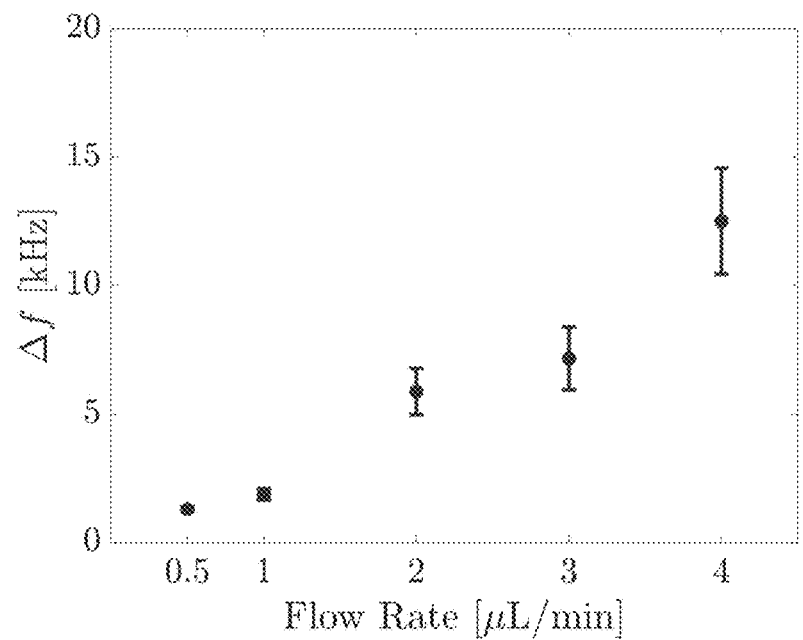
FIG. 11: Minimum sensitivity level of third mechanism, wherein from reset fluid flow, the minimum resolvable flow rate turns out to be 0.5 µL/min and response of 0.4 µL/min is buried in the noise.

In this invention, it has been investigated that the response of the subject-matter of the device from reset condition (where there is no fluid flow) to target flow rate while monitoring the resonance frequency of the microwave sensor (FIG. 5). When the flow rate reaches to target value, sharp upward shifts in the resonance are observed. Each of these shifts depends on the magnitude of the flow rate (FIG. 5b). Therefore, the amount of frequency shift can be used as a sensing parameter for the target flow rate (which constitutes the third mechanism). The baseline frequency fluctuations are about ~1 kHz, from which one can extrapolate a sensitivity level of 0.5 µL/min which is on a par with the first mechanism (FIG. 11). However, as shown with the error bars of FIG. 5b, repeating the experiment at the same flow rate results in a dispersion in the frequency shifts larger the baseline frequency noise.

A third mechanism for the invention is where the fluid flow was given from reset flow conditions, and the deflection amount with respect to the reset flow condition is measured using the microwave resonator. In this third mechanism, the fluid was off initially and then enabled while the resonance frequency of the resonator was tracked simultaneously. For these experiments, another chip with different membrane dimensions was fabricated. This third mechanism of the sensor is similar to a mechanism reported recently in the literature which used PDMS [30], a polymer, rather than $Si_3N_3$ which is a crystalline material. The advantage of using a crystalline material is that owing to large elastic modulus and lower inherent mechanical dissipation, crystalline materials can respond to mechanical stimulus faster and with little to no hysteresis compared to polymeric materials. As such, the sensor demonstrated here exhibits much superior time resolution, as its response exhibits almost no relaxation time in response to abrupt changes in flow rate, whereas the PDMS membrane sensor needs a relaxation time of 180 seconds during which flow rate cannot be updated. The low mechanical loss modulus of silicon nitride, which forms the membrane, is deemed critical for the observed rapid recovery times. Moreover, the lower deflection amount of the nitride membrane compared to PDMS when it is exposed to pressure leads to faster recovery from deflection amount. In the present invention, in order to explain the sensor's relaxation behavior, the phase response of the resonator was examined (FIG. 5c-d). As the nanomembrane integrated sensor is equipped with a measurement system based on phase-sensitive detection, the phase of the resonator can immediately respond to disturbance induced by fluid flow (FIG. 5c). As indicated by a recovery time of several seconds, the sensor can effectively be kept at resonance with a negligible amount of relaxation (FIG. 5d).

In FIG. 7, applied pressure delivers fluid to the target region through a reference flow sensor. Simultaneously, with an external heterodyne circuitry, the response of the microwave resonator is measured by phase sensitive detection performed by a lock in amplifier.

Figure 8:
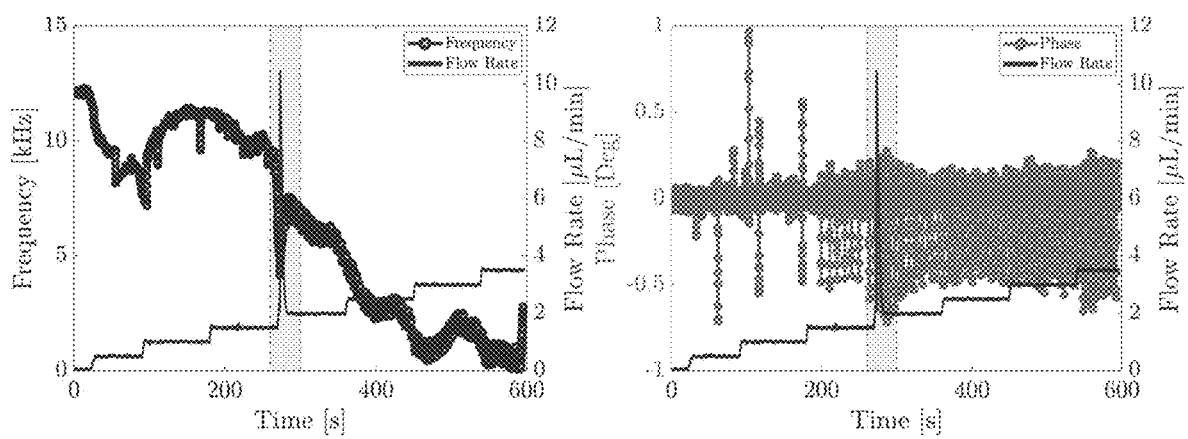
FIG. 8: An example of phase and frequency change of the resonator recorded with a device having a relatively large membrane (1.5 mm×0.3 mm×220 nm, length×width×thickness, respectively).

In FIG. 8, flow rate is increased with an incremental step of 0.5 µL/min. The shaded region shows an abrupt change in the flow rate up to 10 µL/min, yet the subject-matter of flow rate sensor also responses to it with an increasing pulsations rate which turns to normal after the flow rate is settled.

Figure 9:
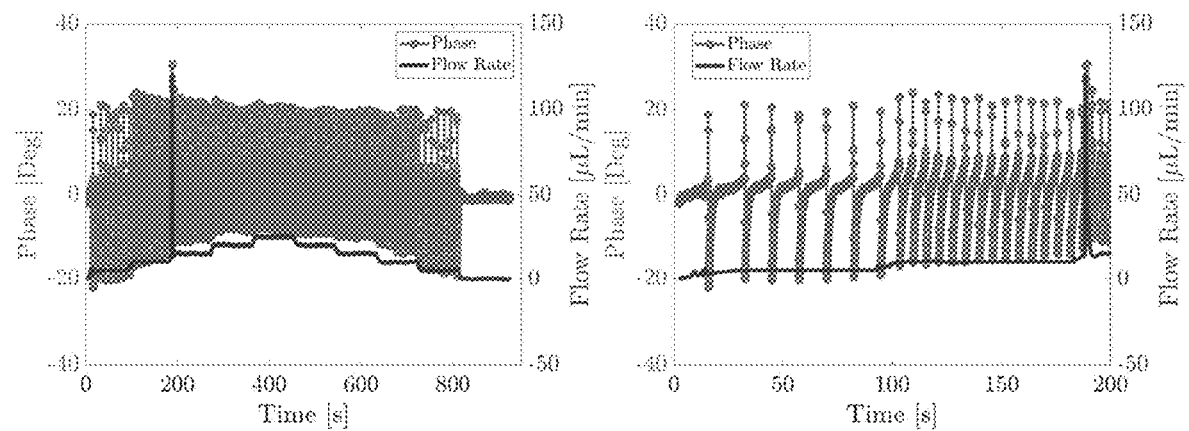
FIG. 9: An example of phase change of the resonator recorded with a device having a relatively smaller membrane (800 µm×350 µm×220 nm, length×width×thickness, respectively).

In FIG. 9, the flow rate is increased with steps of 5 µL/min until 25 µL/min. Pulsation intervals get narrower as the flow rate increases. A zoomed window to the first 350 seconds is also illustrated.

In FIG. 10, the results for the second mechanism are shown, where the pulsation frequency changes with respect to flow rate are depicted.

In FIG. 11, the results of the third mechanism are shown as the frequency change of the microwave resonator with respect to the applied flow rate.

Figure 12:
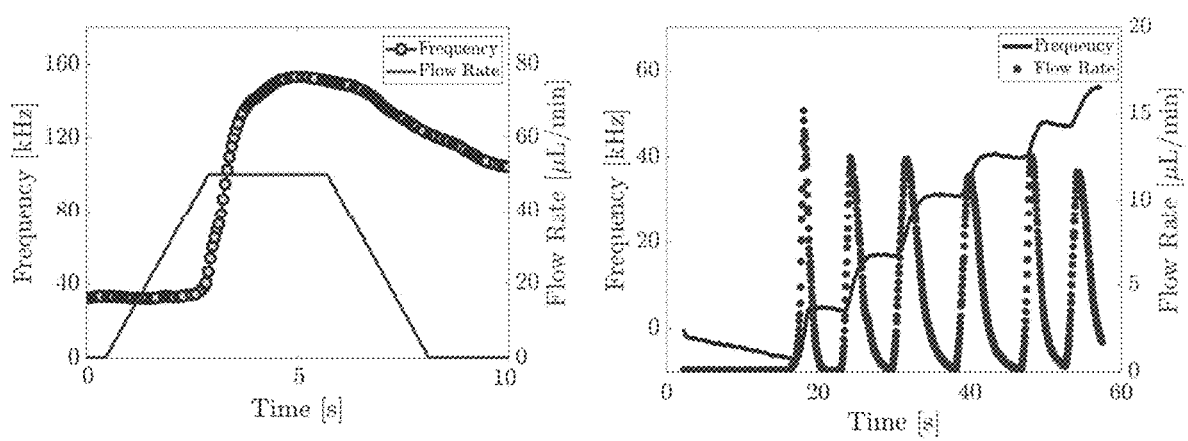
FIG. 12: (a) An example of the third mechanism, the frequency response from a reset condition, (b) Frequency response when the flow is on and off continuously.
Figure 13:
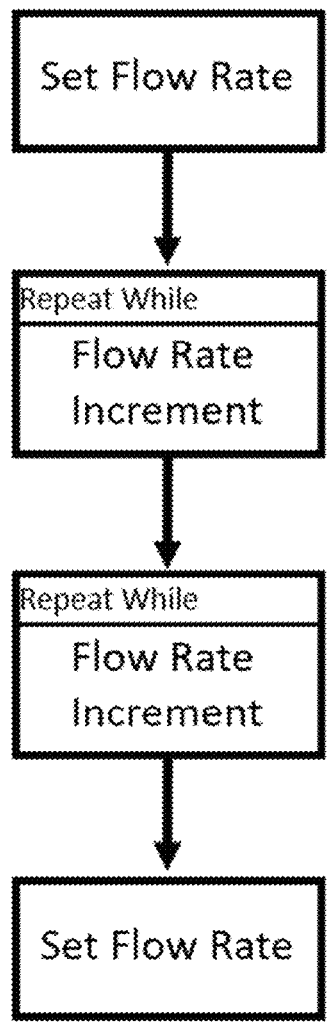
FIG. 13: An example of block diagram used for controlling flow rate sensor via Fluigent software (The software sets the flow rate to a certain value by arranging the applied pressure from the channel.)

In FIG. 12, further results of the third mechanism are shown. In FIG. 12a, the flow rate is set manually by arranging the applied pressure to target flow rate value and pressure was on until frequency response saturates. There is a downward drift in the frequency after the flow is off. In FIG. 12b, the flow rate is set by the Fluigent software. Average of the frequency shift is 10 kHz with a dispersion of 1.5 kHz.

Figure 14:
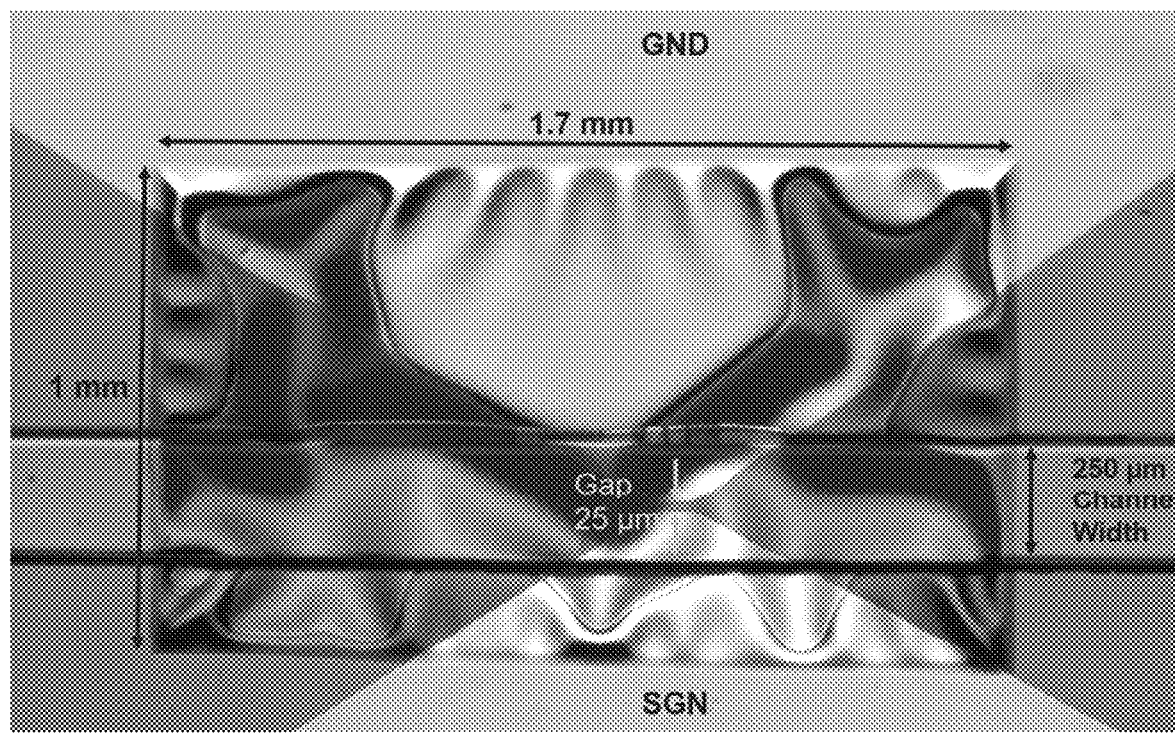
FIG. 14: Fabricated membrane that has width of 1 mm and length of 1.7 mm, two sensing electrodes that are 25 µm apart were aligned on top of 220 nm thick silicon nitride membrane.

In one embodiment of the invention, additional experiments have been carried on pressurizing air instead of DI water. Subject-matter of microwave resonators plays an important role as a flow rate sensor in ventilation machines. Thus, the device subject to the present invention can be used for the treatment of COVID-19 pandemic. In one embodiment, the membrane that is fabricated for this purpose has the following dimensions of 1.7 mm×1 mm×220 nm (FIG. 14). Two sensing electrodes were aligned 25 µm apart and its resonance frequency was tracked at 2.54 GHz with an Allan deviation of $4\times10^{-8}$. Although the micrograph in FIG. 14 shows a device where the microchannel width is smaller than the membrane dimensions, other geometries can be envisaged such as one in which the membrane and the microchannel have similar widths, and another one where the microchannel is wider than the membrane to be used as air flow sensors with different characteristics as well.

Figure 15:
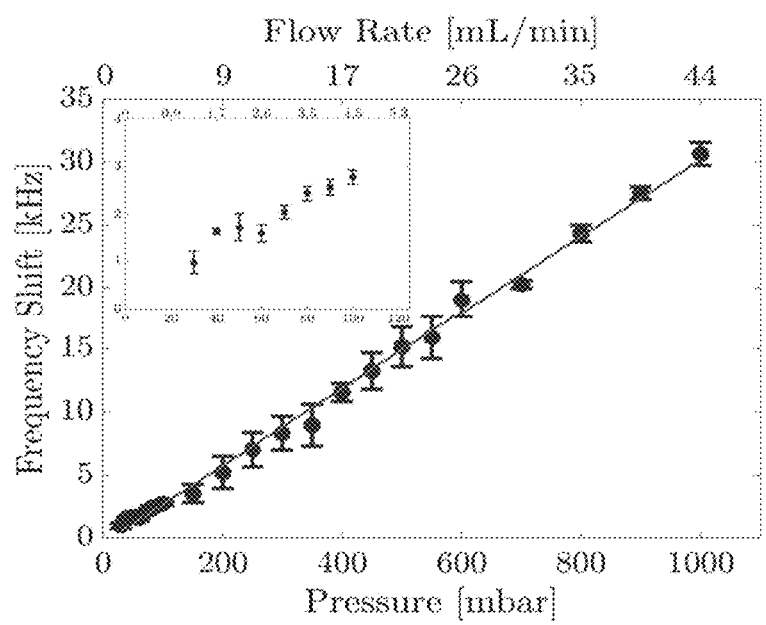
FIG. 15: Frequency shift vs applied pressure as the air was pressurized through the microchannel.

Similar to previous experiments with the liquid flow, using the third mechanism where the flow is given from the reset condition, it is investigated the frequency response of the mechanism of the subject-matter of the device in the interval of 0-45 mL/min (FIG. 15). While the same experimental setup and measurement technique was utilized, another chip with different membrane dimensions was fabricated following the same nanofabrication techniques. The relation between the flow rate and the induced frequency shift (FIG. 15) is almost linear. At low flow rate values (inset figure) this linearity is partially lost. However, at higher flow rates, a linear relation is more visible. The overall trend in FIG. 15 is increasing as the applied pressure increases. However, at low flow rate values this trend is less resolute.

In fact, for some flow rate values, linearity collapses (FIG. 15 inset). With the reported frequency stability, the minimum distinguishable applied pressure value is 30 mbar that corresponds to 0.9 mL/min. The frequency shift, when 20 mbar is applied, is lost in the noise level.

REFERENCES

1. Sader, J. E.; Burg, T. P.; Manalis, S. R. Journal of fluid mechanics 2010, 650, 215-250.
2. Kang, J. H.; Miettinen, T. P.; Chen, L.; Olcum, S.; Katsikis, G.; Doyle, P. S.; Manalis, S. R. Nature methods 2019, 16, (3), 263-269.
3. Burg, T. P.; Sader, J. E.; Manalis, S. R. Physical review letters 2009, 102, (22), 228103.
4. Ekinci, K. L.; Yakhot, V.; Rajauria, S.; Colosqui, C.; Karabacak, D. Lab on a Chip 2010, 10, (22), 3013-3025.
5. Kara, V.; Sohn, Y.-I.; Atikian, H.; Yakhot, V.; Loncar, M.; Ekinci, K. L. Nano letters 2015, 15, (12), 8070-8076.
6. Sader, J. E. Journal of applied physics 1998, 84, (1), 64-76.
7. Argentina, M.; Mahadevan, L. Proceedings of the National Academy of Sciences 2005, 102, (6), 1829-1834.
8. Watanabe, Y.; Suzuki, S.; Sugihara, M.; Sueoka, Y. Journal of fluids and Structures 2002, 16, (4), 529-542.
9. Eloy, C.; Souilliez, C.; Schouveiler, L. Journal of fluids and structures 2007, 23, (6), 904-919.
10. Cetin, A. E.; Stevens, M. M.; Calistri, N. L.; Fulciniti, M.; Olcum, S.; Kimmerling, R. J.; Munshi, N. C.; Manalis, S. R. Nat. Commun. 2017, 8, (1), 1613.
11. Stevens, M. M.; Maire, C. L.; Chou, N.; Murakami, M. A.; Knoff, D. S.; Kikuchi, Y.; Kimmerling, R. J.; Liu, H.; Haidar, S.; Calistri, N. L. Nature biotechnology 2016, 34, (11), 1161-1167.
12. Ward, T.; Faivre, M.; Abkarian, M.; Stone, H. A. Electrophoresis 2005, 26, (19), 3716-3724.
13. Garstecki, P.; Fuerstman, M. J.; Stone, H. A.; Whitesides, G. M. Lab on a Chip 2006, 6, (3), 437-446.
14. Glawdel, T.; Elbuken, C.; Ren, C. L. Physical Review E 2012, 85, (1), 016322.
15. Kuo, J. T.; Yu, L.; Meng, E. Micromachines 2012, 3, (3), 550-573.
16. Baldwin, A.; Yu, L.; Meng, E. Journal of Microelectromechanical Systems 2016, 25, (6), 1015-1024.
17. Kim, J.; Cho, H.; Han, S.-I.; Han, A.; Han, K.-H. Sensors and Actuators B: Chemical 2019, 288, 147-154.
18. Lin, W.-C.; Burns, M. A. Analytical Methods 2015, 7, (9), 3981-3987.
19. Wissman, J. P.; Sampath, K.; Freeman, S. E.; Rohde, C. A. Sensors 2019, 19, (11), 2639.
20. Alfadhel, A.; Li, B.; Zaher, A.; Yassine, O.; Kosel, J. Lab on a Chip 2014, 14, (22), 4362-4369.
21. Tang, M.; Liu, F.; Lei, J.; Ai, Z.; Hong, S.-L.; Zhang, N.; Liu, K. Microfluidics and Nanofluidics 2019, 23, (11), 118.
22. Chen, Z.; Guo, Z.; Mu, X.; Li, Q.; Wu, X.; Fu, H. Optics Express 2019, 27, (25), 36932-36940.
23. Salipante, P.; Hudson, S. D.; Schmidt, J. W.; Wright, J. D. Experiments in Fluids 2017, 58, (7), 85.
24. Stern, L.; Bakal, A.; Tzur, M.; Veinguer, M.; Mazurski, N.; Cohen, N.; Levy, U. Sensors 2014, 14, (9), 16799-16807.
25. Campagnolo, L.; Nikolić, M.; Perchoux, J.; Lim, Y. L.; Bertling, K.; Loubiere, K.; Prat, L.; Rakić, A. D.; Bosch, T. Microfluidics and Nanofluidics 2013, 14, (1-2), 113-119.
26. Cheri, M. S.; Latifi, H.; Sadeghi, J.; Moghaddam, M. S.; Shahraki, H.; Hajghassem, H. Analyst 2014, 139, (2), 431-438.
27. Noeth, N.; Keller, S. S.; Boisen, A. Sensors 2014, 14, (1), 229-244.
28. Zhang, Q.; Ruan, W.; Wang, H.; Zhou, Y.; Wang, Z.; Liu, L. Sensors and Actuators A: Physical 2010, 158, (2), 273-279.
29. Węglarski, M.; Jankowski-Mihutowicz, P.; Pitera, G.; Jurków, D.; Dorczyński, M. Sensors 2020, 20, (1), 268.
30. Zarifi, M. H.; Sadabadi, H.; Hejazi, S. H.; Daneshmand, M.; Sanati-Nezhad, A. Scientific reports 2018, 8, (1), 1-10.
31. Maenhout, G.; Bao, J.; Markovic, T.; Ocket, I.; Nauwelaers, B. In Reliable, Fast and Reusable Interfacing of High-Frequency Signals to Disposable Lab-on-a-Chip Devices, 2019 IEEE MTT-S International Microwave Biomedical Conference (IMBioC), 2019; IEEE: pp 1-4.
32. FRP: flow-rate platform, a microfluidic flow sensor. https://www.fluigent.com/product/microfluidic-components-3/frp-flow-rate-platform/. (27.02.2020),
33. Chuhuan, F.; Fan, S.; Jian, S.; Qi, L.; Hongbin, Y. Ieee Photonics Journal 2017, 9, (4), 1-9.

The invention claimed is:

1. A flow rate sensor for fluids having high sensitivity of flow rate, characterized by comprising;
    a microfluidic flow channel (17) wherein the fluid flow passes through,
    a nanomembrane (15) which forms part of one of the walls of a microfluidic flow channel (17), so that the fluidic flow rate on the microfluidic flow channel (17) induces deflection on the nanomembrane (15);
    a microwave resonator overlapping partially or entirely with the nanomembrane, so that the deflection of the nanomembrane changes the capacitance, and therefore resonance frequency, of the microwave sensors, and this way they can be converted into electronic signals,
    where any of three different parameters related to the deflections of the nanomembrane can be used as flow sensing parameters:
    i. an instability of the nanomembrane at constant flow rate, where the instability takes the form of periodic deformations and deflections of the nanomembrane, where the period of the deformation is determined by the flow rate.
    ii. an instability of the nanomembrane at constant flow rate, where the instability takes the form of periodic deformations and deflections of the nanomembrane, where the amplitude of the deformation is determined by the flow rate.
    iii. A sudden deflection of the nanomembrane, after a sudden change between reset flow conditions and set flow conditions is applied, where the deflection amount is determined by the flow rate.

2. A flow rate sensor according to claim 1 wherein the microwave resonator has the form of a coplanar waveguide resonator.

3. A flow rate sensor according to claim 1, wherein the materials used are PDMS for the top and side walls of the microfluidic flow channel; Silicon Nitride for the nanomembrane (in places where Silicon Nitride is suspended), and the bottom wall of the microfluidic channel (in places where Silicon Nitride is supported by Silicon underneath); Silicon as the structural support material for the device, and Gold for defining the signal and ground electrodes of the microwave resonator, thereby the flow rate sensor is biocompatible, non-contact and non-intrusive.

4. A flow rate sensor according to claim 1, wherein the flow sensor shows sensitivity to minimum rate change increment of 0.1 μL/min with lowest detection limit of between 0.4-0.5 μL/min.

5. A flow rate sensor according to claim 1, wherein dimensions of the microfluidic flow channel (17) is in the range of 1-300 μmin width and 1-150 μmin depth.

6. An operation method of flow rate sensor according to claim 1, characterized by comprising following steps;
   i. a calibration curve for the flow rate sensor is obtained in a calibration setup where the fluid of interest passes through an independent flow rate controller and the flow rate sensor,
   ii. different values of the fluid flow are set, and for each flow rate, the oscillation frequency and amplitude of the nanomembrane (15), as they modulate the frequency of the microwave sensor, are recorded, to obtain the calibration curve,
   iii. the calibrated flow rate sensor is then disconnected from the calibration setup, and is connected to the desired flow path,
   iv. the period and/or amplitude of the pulsations as detected by the microwave sensors are then converted into flow rate values using the calibration curve.

7. An operation method of flow rate sensor according to claim 1, characterized by comprising following steps;
   i. a calibration curve for the flow rate sensor is obtained in a calibration setup where the fluid of interest passes through an independent flow rate controller and the flow rate sensor,
   ii. the fluid flow is alternated between a reset value and set value, for a different range of set values. For each cycle, the deformation amount of the nanomembrane (15) is measured by the microwave sensor to obtain a calibration curve,
   iii. the calibrated flow rate sensor is then disconnected from the calibration setup, and is connected to the desired flow path,
   iv. when the flow rate in the desired flow path changes from reset flow rate to set flow rate, the resulting deformation amount of the nanomembrane is detected by the microwave sensors which is then converted into a flow rate value using the calibration curve.

* * * * *